US008876204B1

(12) United States Patent
Jewett

(10) Patent No.: US 8,876,204 B1
(45) Date of Patent: Nov. 4, 2014

(54) MULTI-PURPOSE SUPPORT ASSEMBLY

(76) Inventor: Edward E. Jewett, Crown Point, IN (US)

( * ) Notice: Subject to any disclaimer, the term of this patent is extended or adjusted under 35 U.S.C. 154(b) by 163 days.

(21) Appl. No.: 13/586,983

(22) Filed: Aug. 16, 2012

(51) Int. Cl.
*A47C 7/62* (2006.01)

(52) U.S. Cl.
USPC ............... 297/188.1; 297/188.08; 297/188.09

(58) Field of Classification Search
CPC ....... A47K 3/281; A47K 3/282; A47K 13/00; A47K 13/005; A47K 17/00
USPC .............................. 297/188.08, 188.09, 188.1
See application file for complete search history.

(56) References Cited

U.S. PATENT DOCUMENTS

| | | | |
|---|---|---|---|
| 3,638,647 A * | 2/1972 | Creelman | 5/89.1 |
| 3,936,109 A * | 2/1976 | Richardson | 312/223.5 |
| 4,319,367 A * | 3/1982 | Cantillo | 4/353 |
| 5,071,192 A | 12/1991 | Adler | |
| 5,551,100 A | 9/1996 | Kindrick | |
| 5,640,723 A * | 6/1997 | Stanek | 4/578.1 |
| 5,940,900 A * | 8/1999 | Wells | 4/515 |
| 6,089,395 A | 7/2000 | Karttunen et al. | |
| 6,408,456 B1 | 6/2002 | Fike et al. | |
| 6,615,420 B1 | 9/2003 | Hyden et al. | |
| 6,840,180 B2 * | 1/2005 | Ulmer | 108/13 |
| 6,854,803 B2 * | 2/2005 | Tomas et al. | 297/423.41 |
| D519,291 S | 4/2006 | Higgs et al. | |
| D536,889 S | 2/2007 | Self et al. | |
| 7,810,180 B2 | 10/2010 | List | |
| 2007/0294816 A1 * | 12/2007 | Cheng | 4/449 |
| 2008/0034494 A1 | 2/2008 | Monteiro | |
| 2012/0169106 A1 * | 7/2012 | Alkhattaf | 297/423.41 |

* cited by examiner

*Primary Examiner* — Philip Gabler

(57) ABSTRACT

A multi-purpose support assembly includes a housing that has a bottom wall and a perimeter wall coupled to and extending upwardly from the bottom wall. A lid is hingedly coupled to the housing. A stop is coupled to and extends upwardly from the perimeter wall of the housing. A shaft is coupled to and extends downwardly from the bottom wall of the housing. A base is coupled to a bottom end of the shaft. The base abuts a support surface so the base may support the housing above the support surface. The base is positionable proximate a toilet so a top of the lid may be accessible to a user seated on the toilet.

14 Claims, 7 Drawing Sheets

MULTI-PURPOSE SUPPORT ASSEMBLY

BACKGROUND OF THE DISCLOSURE

Field of the Disclosure

The disclosure relates to multi-purpose support devices and more particularly pertains to a new multi-purpose support device for supporting multiple objects.

SUMMARY OF THE DISCLOSURE

An embodiment of the disclosure meets the needs presented above by generally comprising a housing that has a bottom wall and a perimeter wall coupled to and extending upwardly from the bottom wall. A lid is hingedly coupled to the housing. A stop is coupled to and extends upwardly from the perimeter wall of the housing. A shaft is coupled to and extends downwardly from the bottom wall of the housing. A base is coupled to a bottom end of the shaft. The base abuts a support surface so the base may support the housing above the support surface. The base is positionable proximate a toilet so a top of the lid may be accessible to a user seated on the toilet.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
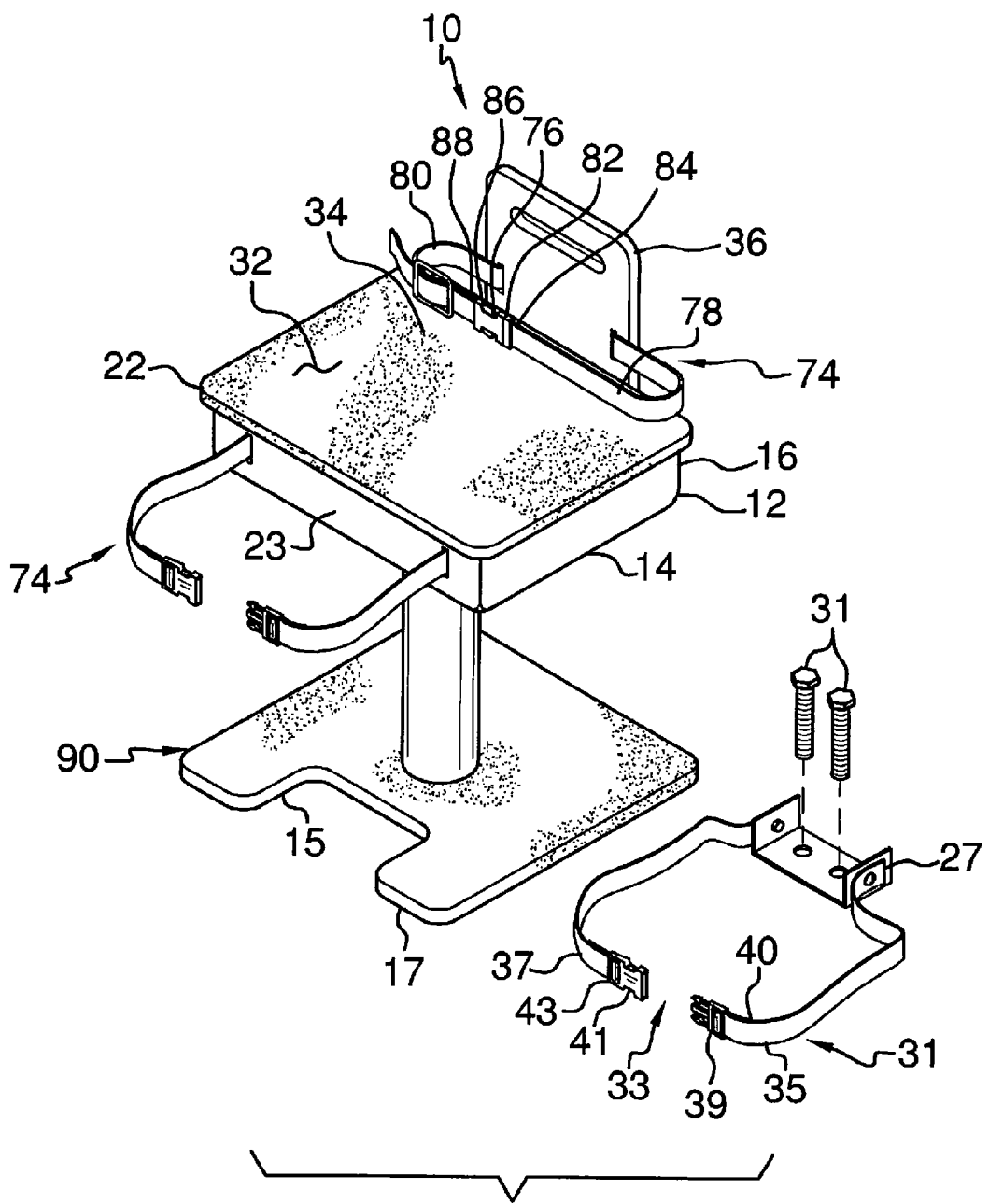
FIG. 1 is a perspective view of a multi-purpose support assembly according to an embodiment of the disclosure.
Figure 2:
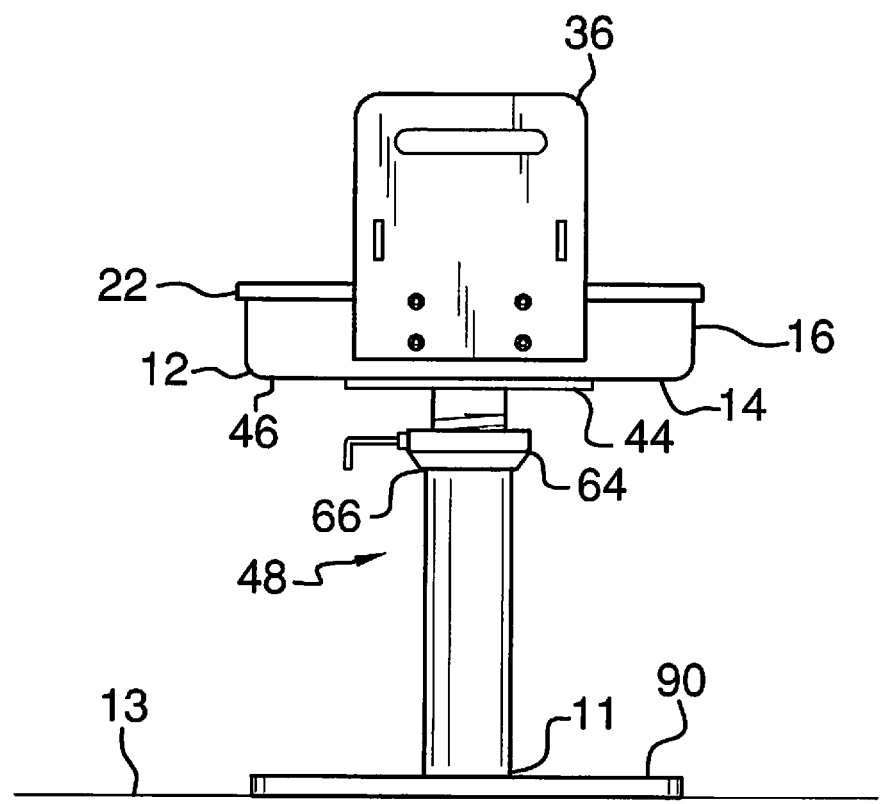
FIG. 2 is a back view of an embodiment of the disclosure.
Figure 3:
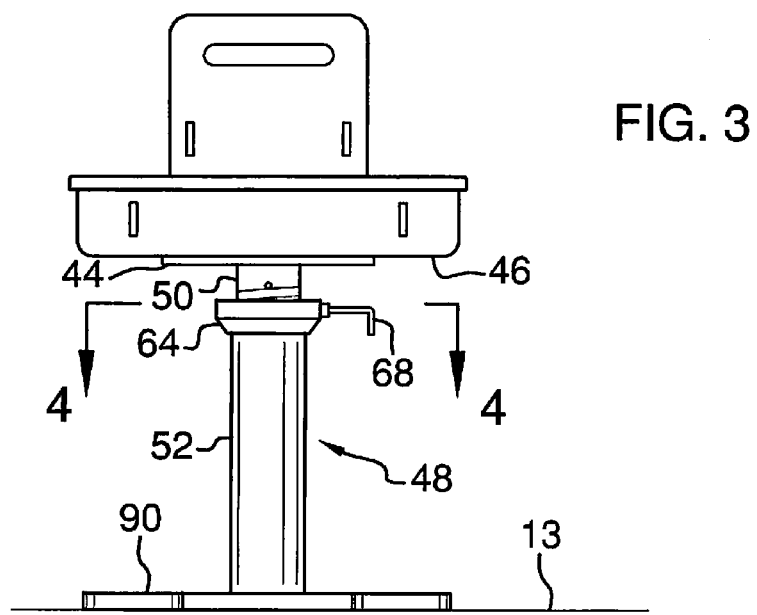
FIG. 3 is a front view of an embodiment of the disclosure.
Figure 4:
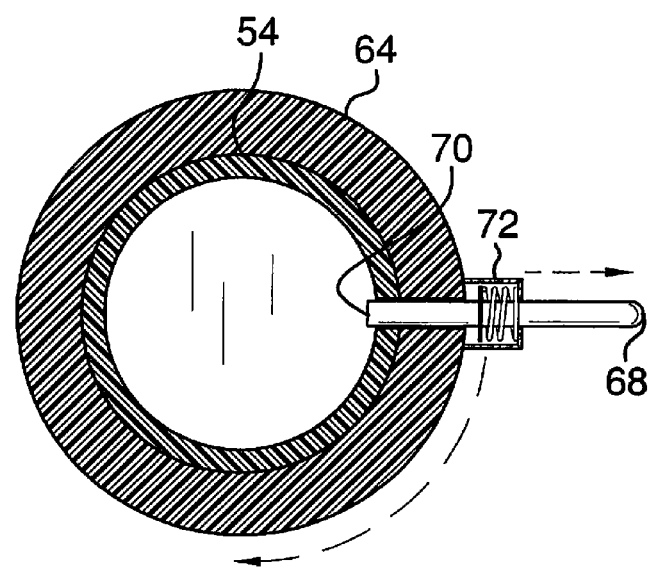
FIG. 4 is a cross-sectional view taken along line 4-4 of FIG. 3 of an embodiment of the disclosure.
Figure 5:
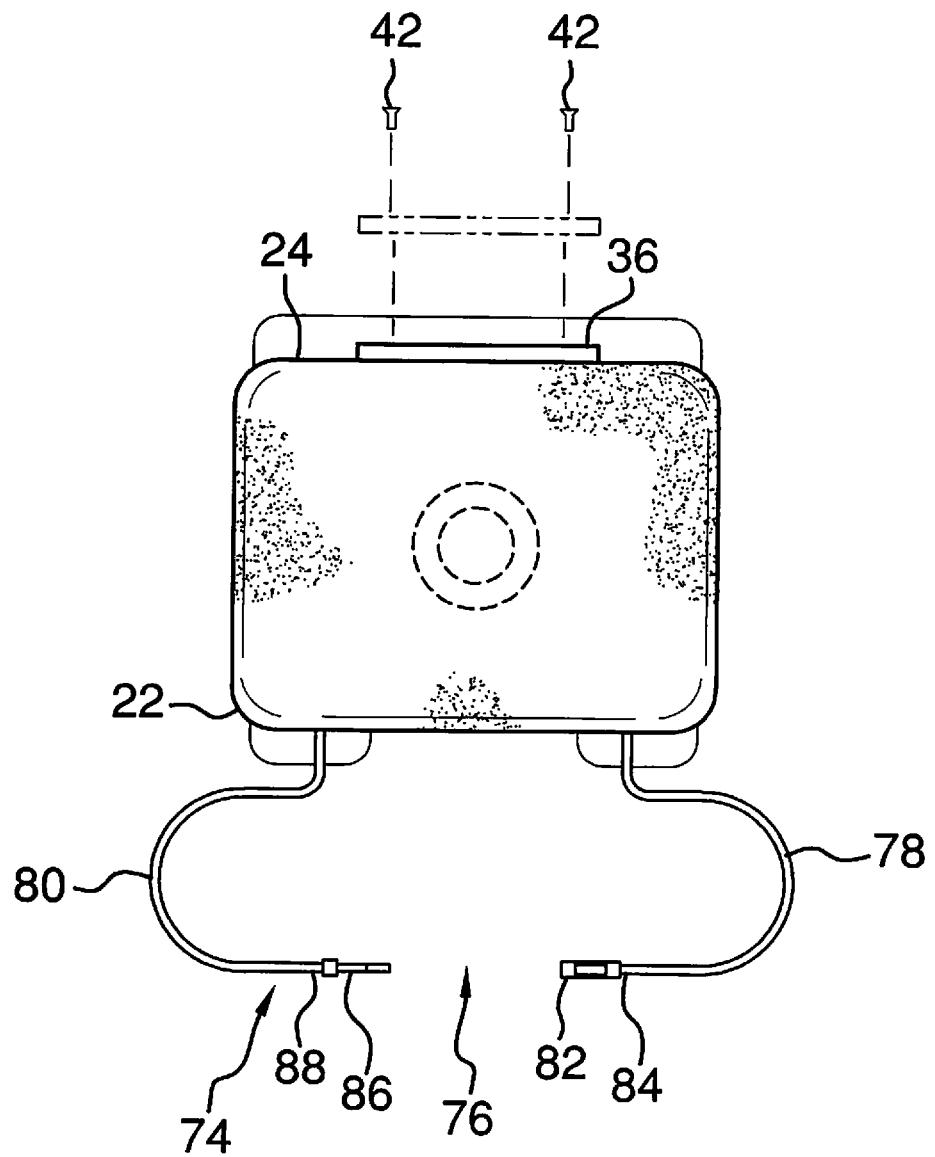
FIG. 5 is a top view of an embodiment of the disclosure.
Figure 6:
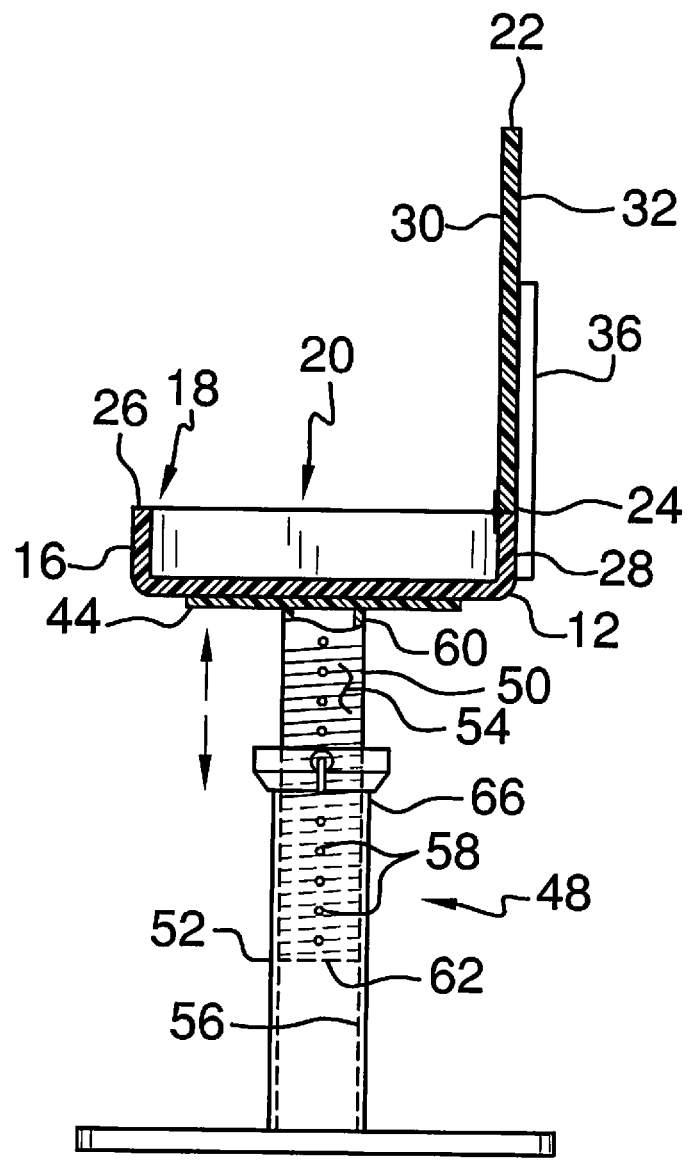
FIG. 6 is a cut away view of an embodiment of the disclosure.
Figure 7:
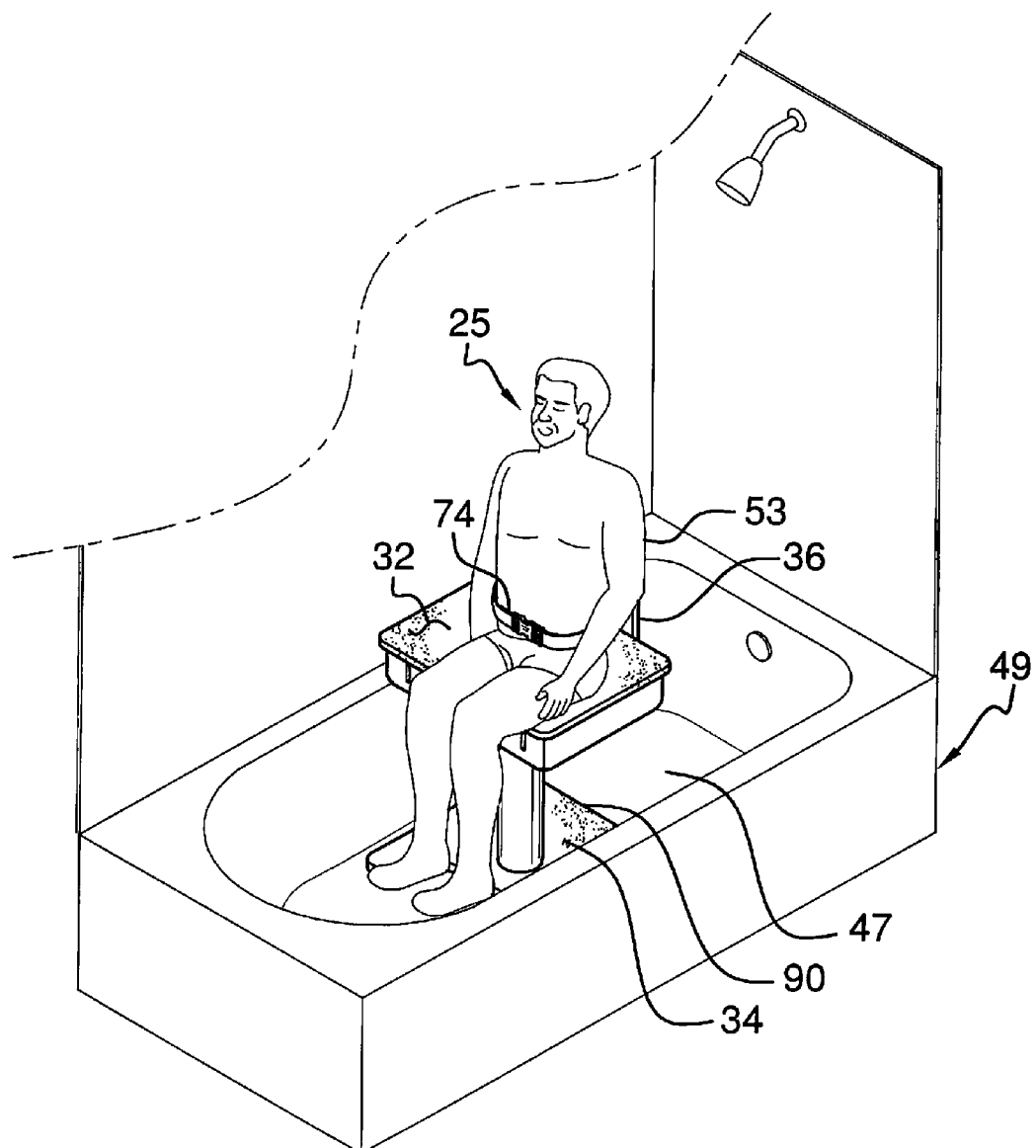
FIG. 7 is an in use view of an embodiment of the disclosure.
Figure 8:
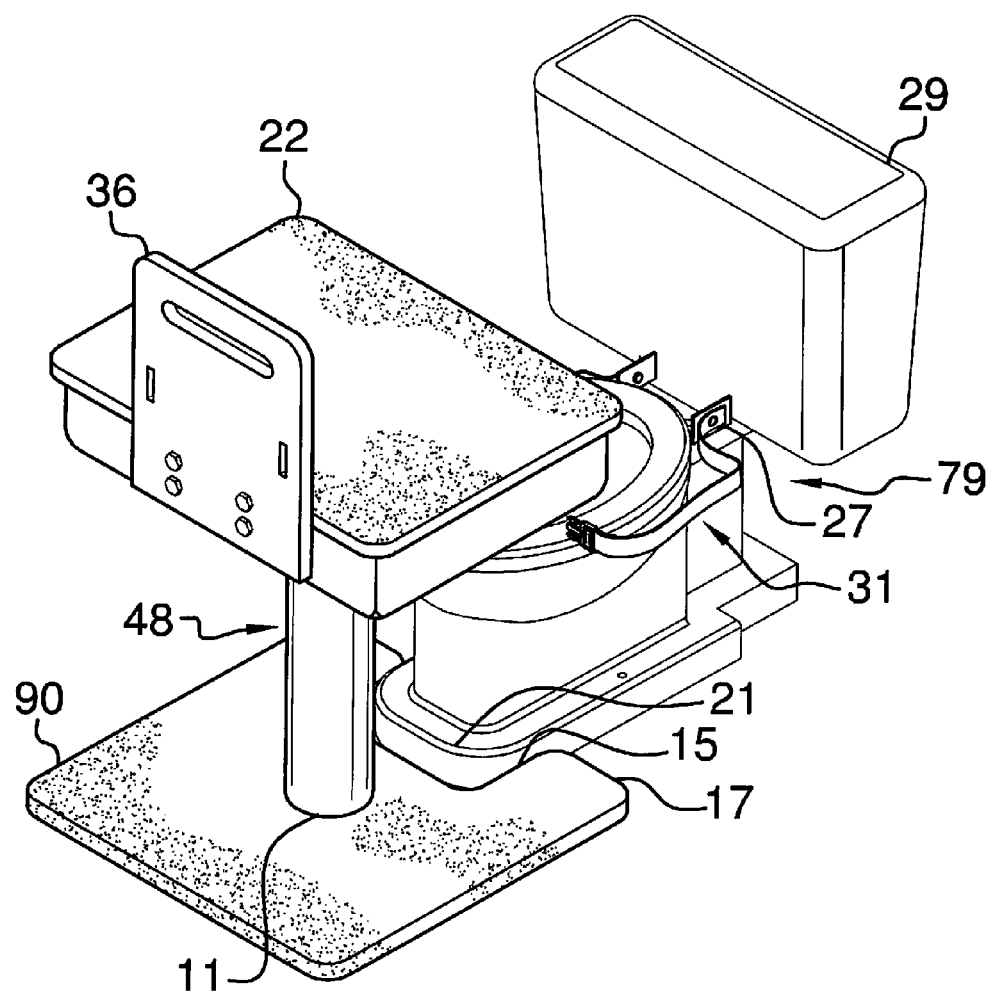
FIG. 8 is a top front side perspective view of an embodiment of the disclosure.

With reference now to the drawings, and in particular to FIGS. 1 through 8 thereof, a new multi-purpose support device embodying the principles and concepts of an embodiment of the disclosure and generally designated by the reference numeral 10 will be described.

As best illustrated in FIGS. 1 through 7, the multi-purpose support assembly 10 generally comprises a housing 12 has a bottom wall 14 and a perimeter wall 16 coupled to and extending upwardly from the bottom wall 14. A top 18 of the perimeter wall 16 of the housing 12 defines an opening 20 to access an interior of the housing 12. The housing 12 may be comprised of a fluid impermeable material. The housing 12 may have a width between 76 cm and 106 cm and a length between 46 cm and 61 cm.

A lid 22 is coupled to the housing 12. A rear edge 24 of the lid 22 is hingedly coupled to a top edge 26 of the perimeter wall 16 proximate a rear side 28 of the perimeter wall 16 of the housing 12 so the lid 22 may cover the housing 12. The lid 22 is positionable in a closed position that has a bottom surface 30 of the lid 22 abutting the top edge 26 of the perimeter wall 16 of the housing 12. The lid 22 may support an object on a top surface 32 of the lid 22. The lid 22 is positionable in an open position that has the lid 22 extending upwardly from the perimeter wall 16 of the housing 12. The lid 22 may have a width between 80 cm and 110 cm and a length between 50 cm and 66 cm. The lid 22 may be comprised of a fluid impermeable material. The lid 22 may have an outer coating 34 comprised of a resiliently compressible material such as rubber or other similar material.

A stop 36 is coupled to and extends upwardly from the rear side 28 of the perimeter wall 16 of the housing 12 proximate the rear edge 24 of the lid 22. The stop 36 may prevent an object from sliding rearwardly off of the lid 22 when the lid 22 is positioned in the closed position. The stop 36 may be comprised of a fluid impermeable material. A pair of fasteners 42 may extend through the stop 36 and engage the housing 12 to retain the stop 36 on the housing 12.

A plate 44 is coupled to a bottom surface 46 of the housing 12. A shaft 48 is coupled to and extends downwardly from the plate 44. The shaft 48 includes a top portion 50 and a bottom portion 52. An outer surface 54 of the top portion 50 threadably engages an inner surface 56 of the bottom portion 52 so the shaft 48 may have a selectively adjustable height.

A plurality of spaced retainer apertures 58 extends through the top portion 50 of the shaft 48. The spaced retainer apertures 58 are spaced along a longitudinal axis extending through a top end 60 and a bottom end 62 of the top portion 50 of the shaft 48. A coupler 64 is coupled to a top end 66 of the bottom portion 52 of the shaft 48. The coupler 64 comprises a closed loop so the coupler 64 may insertably receive the top portion 50 of the shaft 48.

A retainer 68 is movably coupled to the coupler 64 so the retainer 68 extends laterally through the coupler 64. An engaging end 70 of the retainer 68 selectively extends through a selected one of the retainer apertures 58 so the retainer 68 may retain the top portion 50 of the shaft 48 at the selected height. A biasing member 72 is positioned around the retainer 68. The biasing member 72 biases the engaging end 70 through the selected one of the retainer apertures 58. The engaging end 70 of the retainer 68 may be drawn outwardly from the selected retainer aperture 58 so the top portion 50 of the shaft 48 may be positioned at the selected height.

A belt 74 is removably coupled to the stop 36. The belt 74 has a break 76 therein defining a first portion 78 and a second portion 80 of the belt 74. A first coupler 82 is coupled to a free end 84 of the first portion 78 of the belt 74. A second coupler 86 is coupled to a free end 88 of the second portion 80 of the belt 74. The first 78 and second 80 couplers are complementary so the first 78 and second 80 portions of the belt 74 may form a closed loop.

A base 90 is coupled to a bottom end 11 of the shaft 48. The base 90 abuts a support surface 13 so the base 90 may support the housing 12 above the support surface 13. The base 90 has a groove 15 extending inwardly from a forward edge 17 of the base 90. The base 90 is positionable proximate a toilet 19 so the groove 15 may insertably receive a base 21 of the toilet 19 so lid 22 may be used as a desk. The belt 74 may be removed from the stop 36 to be removably coupled to a front side 23 of the housing 12 when the base 90 is positioned proximate the toilet 19 so the belt 74 may retain a user 25 on the toilet 19.

A mount 27 is coupled to the toilet 19. The mount 27 is positioned proximate a tank 29 on the toilet 19. A pair of fasteners 31 may extend through the mount 27 and engage the toilet 19 to retain the mount 27 on the toilet 19. A strap 31 is coupled to the mount 27. The strap 31 has a break 33 therein defining a first portion 35 and a second portion 37. A first fastener 39 is coupled to a free end 40 of the first portion 35 of the strap 31. A second fastener 41 is coupled to a free end 43 of the second portion 45 of the strap 31. The second fastener 41 is complimentary to the first fastener 39 so the first 35 and second 45 portions of the strap 31 may form a closed loop. The strap 31 is positionable around the user 25 when the user 25 sits on the toilet 19.

The base 90 is positionable on a bottom 47 of a tub 49 so the lid 22 may support the user 25 sitting on the upper surface 32 of the lid 22. The stop 36 may abut the user's back 53 when the user 25 sits on the lid 22. The belt 74 may be positionable around the user 25 when the user 25 sits on the lid 22 so the first fastener 39 engages the second fastener 41. The belt 74 may retain the user 25 on the lid 22. The base 90 may be comprised of a fluid impermeable material. The base 90 may have an outer coating 34 comprised of a resiliently compressible material such as rubber or other similar material.

In use, the base 90 may be positioned proximate the toilet 19 so the lid 22 may be used as a desk. The belt 74 may be removably coupled to the front side 23 of the housing 12 to assist a user 25 with toilet training. The mount 27 may be coupled to the toilet 19 so the strap 31 may retain the user 25 on the toilet 19 if the user needs physical assistance to stay on the toilet 19. The base 90 may be positioned in the tub 49 so the lid 22 may be used as a seat. The user 25 may sit on the lid 22 if the user 25 needs physical assistance in bathing. The belt 74 may be removably coupled to the stop 36 so the belt 74 may retain the user 25 on the lid 22 while bathing.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A multi-purpose support assembly comprising:
   a housing having a bottom wall and a perimeter wall coupled to and extending upwardly from said bottom wall;
   a lid hingedly coupled to said housing;
   a stop coupled to and extending upwardly from said perimeter wall of said housing;
   a shaft coupled to and extending downwardly from said bottom wall of said housing;
   a base coupled to a bottom end of said shaft, said base abutting a support surface whereby said base is configured to support said housing above the support surface, said base being positionable proximate a toilet whereby a top of said lid is configured to be accessible to a user seated on said toilet
   said base having a groove extending inwardly from a forward edge of said base;
   said base being positionable proximate said toilet whereby said groove is configured to insertably receive a base of said toilet, whereby said lid is configured to be used as a desk;
   a belt coupled to said stop, said belt having a break therein defining a first portion and a second portion of said belt;
   a first coupler coupled to a free end of said first portion of said belt;
   a second coupler coupled to a free end of said second portion of said belt, said first and second couplers being complementary whereby said first and second portions of said belt are configured to form a closed loop; and
   said base being positionable on a bottom of a tub whereby said lid is configured to support a user sitting on an upper surface of said lid, whereby said stop is configured to abut the user's back, whereby said belt is configured to be positionable around the user when the user sits on said lid having said first fastener engaging said second fastener whereby said belt is further configured to retain the user on said lid.

2. The assembly according to claim 1, further including a top of said perimeter wall of said housing defining an opening to access an interior of said housing.

3. The assembly according to claim 1, further including a rear edge of said lid being hingedly coupled to a top edge of said perimeter wall proximate a rear side of said perimeter wall of said housing whereby said lid is configured to cover said housing.

4. The assembly according to claim 3, further including said lid being positionable in a closed position having a bottom surface of said lid abutting said top edge of said perimeter wall of said housing whereby said lid is configured to support an object on a top surface of said lid, said lid being positionable in an open position having said lid extending upwardly from said perimeter wall of said housing.

5. The assembly according to claim 1, further comprising:
   said lid being positionable in a closed position; and
   said stop being coupled to and extending upwardly from a rear side of said perimeter wall of said housing proximate a rear edge of said lid whereby said stop is configured to prevent an object from sliding rearwardly off of said lid when said lid is positioned in said closed position.

6. The assembly according to claim 1, further including a plate coupled to a bottom surface of said housing.

7. The assembly according to claim 6, further including said shaft being coupled to and extending downwardly from said plate.

8. The assembly according to claim 1, further including said shaft including a top portion and a bottom portion, an outer surface of said top portion threadably engaging an inner surface of said bottom portion whereby said shaft is configured to have a selectively adjustable height.

9. The assembly according to claim 1, further comprising:
   said shaft including a top portion and a bottom portion; and
   a coupler coupled to a top end of said bottom portion of said shaft, said coupler comprising a closed loop whereby said coupler is configured to insertably receive said top portion of said shaft.

10. The assembly according to claim 1 further comprising:
    said shaft including a top portion and a bottom portion;

a plurality of spaced retainer apertures extending through said top portion of said shaft, said spaced retainer apertures being spaced along a longitudinal axis extending through a top end and a bottom end of said top portion of said shaft;

a coupler coupled to a top end of said bottom portion of said shaft; and a retainer movably coupled to said coupler, an engaging end of said retainer selectively extending through a selected one of said retainer apertures whereby said retainer is configured to retain said top portion of said shaft at a selected height.

11. The assembly according to claim 1, further including a mount coupled to said toilet, said mount being positioned proximate a tank on said toilet.

12. The assembly according to claim 1, further comprising:
a mount coupled to said toilet; and
a strap coupled to said mount, said strap having a break therein defining a first portion and a second portion;
a first fastener coupled to a free end of said first portion of said strap; and
a second fastener coupled to a free end of said second portion of said strap, said second fastener being complimentary to said first fastener whereby said first and second portions of said strap are configured to form a closed loop.

13. The assembly according to claim 1, further including said base having a groove extending inwardly from a forward edge of said base.

14. A multi-purpose support assembly comprising:
a housing having a bottom wall and a perimeter wall coupled to and extending upwardly from said bottom wall, a top of said perimeter wall of said housing defining an opening to access an interior of said housing, said housing being comprised of a fluid impermeable material;
a lid coupled to said housing, a rear edge of said lid being hingedly coupled to a top edge of said perimeter wall proximate a rear side of said perimeter wall of said housing whereby said lid is configured to cover said housing, said lid being positionable in a closed position having a bottom surface of said lid abutting said top edge of said perimeter wall of said housing whereby said lid is configured to support an object on a top surface of said lid, said lid being positionable in an open position having said lid extending upwardly from said perimeter wall of said housing, said lid being comprised of a fluid impermeable material;
a stop being coupled to and extending upwardly from said rear side of said perimeter wall of said housing proximate a rear edge of said lid whereby said stop is configured to prevent an object from sliding rearwardly off of said lid when said lid is positioned in said closed position, said stop being comprised of a fluid impermeable material;
a plate coupled to a bottom surface of said housing;
a shaft coupled to and extending downwardly from said plate, said shaft including a top portion and a bottom portion, an outer surface of said top portion threadably engaging an inner surface of said bottom portion whereby said shaft is configured to have a selectively adjustable height;

a plurality of spaced retainer apertures extending through said top portion of said shaft, said spaced retainer apertures being spaced along a longitudinal axis extending through a top end and a bottom end of said top portion of said shaft;

a coupler coupled to a top end of said bottom portion of said shaft, said coupler comprising a closed loop whereby said coupler is configured to insertably receive said top portion of said shaft;

a retainer movably coupled to said coupler, an engaging end of said retainer selectively extending through a selected one of said retainer apertures whereby said retainer is configured to retain said top portion of said shaft at a selected height;

a belt coupled to said stop, said belt having a break therein defining a first portion and a second portion of said belt;

a first coupler coupled to a free end of said first portion of said belt;

a second coupler coupled to a free end of said second portion of said belt, said first and second couplers being complementary whereby said first and second portions of said belt are configured to form a closed loop;

a base coupled to a bottom end of said shaft, said base abutting a support surface whereby said base is configured to support said housing above the support surface, said base having a groove extending inwardly from a forward edge of said base, said base being positionable proximate said toilet whereby said groove is configured to insertably receive a base of said toilet, whereby said lid is configured to be used as a desk, said base being positionable on a bottom of a tub whereby said lid is configured to support a user sitting on an upper surface of said lid, whereby said stop is configured to abut the user's back, whereby said belt is configured to be positionable around the user when the user sits on said lid having said first fastener engaging said second fastener whereby said belt is further configured to retain the user on said lid, said base being comprised of a fluid impermeable material;

a mount coupled to said toilet, said mount being positioned proximate a tank on said toilet;

a strap coupled to said mount, said strap having a break therein defining a first portion and a second portion;

a first fastener coupled to a free end of said first portion of said strap; and a second fastener coupled to a free end of said second portion of said strap, said second fastener being complimentary to said first fastener whereby said first and second portions of said strap are configured to form a closed loop, said strap being positionable around the user when the user sits on said toilet having said first fastener engaging said second fastener whereby said strap is configured to retain the user on said toilet.

* * * * *